(12) United States Patent
Jung

(10) Patent No.: US 6,514,957 B1
(45) Date of Patent: Feb. 4, 2003

(54) METHOD OF ALLEVIATING THE VIOLENCE AND STIMULATING THE APPETITE OF STAG IN THE PUBERTY AGE OF THE FALL AND METHOD OF PROMOTING THE GROWTH OF STAG'S HORN

(76) Inventor: Chang-Eun Jung, #564 Shingi-dong, Gongju-city, Choongchungnamdo 314-210 (KR)

(*) Notice: Subject to any disclaimer, the term of this patent is extended or adjusted under 35 U.S.C. 154(b) by 0 days.

(21) Appl. No.: 10/113,160

(22) Filed: Apr. 1, 2002

(30) Foreign Application Priority Data

Dec. 11, 2001 (KR) .......................... 2001-78212

(51) Int. Cl.$^7$ .............................................. A61K 31/56
(52) U.S. Cl. .................. 514/177; 514/177; 514/171; 514/169
(58) Field of Search .................. 514/171, 177

(56) References Cited

PUBLICATIONS

Mundo Salvador, A. (DN 72:9687, CAPLUS, abstract of Rev. Clin. Espan. (1969), 114(1), 53–60).*
Yang et al. (DN 123:247077, CAPLUS, abstract of GOuli Taiwan Daxue Nongxueyuan Yanjiu Baogao (1995), 35(1), 32–44).*
Monfort et al. (DN 123:161120, CAPLUS, abstract of Biol. Reprod. (1995), 53(3), 700–6).*
Ataja et al. (DN 117:83712, CAPLUS abstract of J. Agric. Sci. (1992), 118(3), 371–7).*

* cited by examiner

*Primary Examiner*—Sabiha Qazi
(74) *Attorney, Agent, or Firm*—Wolf, Block, Schorr and Solis-Cohen LLP; Richard P. Gilly

(57) ABSTRACT

A method of alleviating the violence and stimulating the appetite of stags in the puberty age of the fall and a method of allowing to cut and collect more than twice stag's horn is provided by administering 17β-decanoate-4-estrene-3-one and/or 17β-cyclohexylpropionate-4-estrene-3-one.

7 Claims, No Drawings

METHOD OF ALLEVIATING THE VIOLENCE AND STIMULATING THE APPETITE OF STAG IN THE PUBERTY AGE OF THE FALL AND METHOD OF PROMOTING THE GROWTH OF STAG'S HORN

TECHNICAL FIELD

The present invention relates to a method of alleviating the violence and stimulating the appetite of stags in the puberty age of the fall by administering 19-Nortestosterone derivatives, and more particularly, by administering 17β-decanoate-4-estrene-3-one and/or 17β-cyclohexylpropionate-4-estrene-3-one. Further, the present invention relates to a method of allowing to cut and collect more than twice stag's horn by administering 19-Nortestosterone derivatives, and more particularly, by administering 17β-decanoate-4-estrene-3-one and/or 17β-cyclohexylpropionate-4-estrene-3-one to stags after cutting the first horn in the summer.

BACKGROUND ART

In our country, in order to obtain stag's horn, various varieties of deer, red deer and elk have been raised. The growth of stag's horn has deep connection with photoperiod. That is, as the daytime increases, stag's horn drops and new stag's horn comes up, and as the daytime decreases, stag's horn peels off and is matured (cornification). In our country, the first stag's horn comes up in the spring, i.e., March to May and is grown up for 80 to 90 days. Then, in the summer, the grown stag's horn cuts to be collected. The amount, which is obtained from an elk stag in the weight of 500 kg, is approximately 10 kg to 20 kg.

After cutting the first stag's horn, stags are in the puberty age, thereby becoming violent. Stags in the same fold fight with each other, thereby resulting death of about 9 stags among 10 stags. Further, the violent stags in the puberty age scarcely eat anything to starve to death.

In our country, does are raised only to propagate and about 58% of total deer. The self-supply rate of the stag's horn, which is obtained by raising stags, is less than 20% of the total domestic consumption amount. Therefore, more than 80% of the domestic consumption amount is imported from other countries such as New Zealand, Australia, Canada etc., thereby causing outflow of foreign currency. Therefore, the domestic breeders need to conduct researches in order to improve the self-supply rate and the productivity of stag's horn.

A hormone of testosterone is secreted from testicles of stag. This testosterone develops stalk. So, the researches for stimulating the growth of stag's horn and inducing stag's horn by administering testosterone to stag have been developed. However, this conventional method increases the cost due to using hormone. Further, an end of the stalk developed by administering testosterone should cut to differentiate into the horn. Moreover, the administration of testosterone induces the cornification of the horn and increases the contents of crude ash, thereby falling-off the quality of the horn.

DISCLOSURE OF THE INVENTION

Accordingly, an object of the present invention is to alleviate the violence and stimulate the appetite of stags in the puberty age of the fall and to allow to cut and collect more than twice stag's horn by administering 19-Nortestosterone derivatives including 17β-decanoate-4-estrene-3-one and 17β-cyclohexylpropionate-4-estrene-3-one by an oral intake or an injection.

In order to achieve the foregoing and other objects, the present invention provides a method of alleviating the violence and stimulating the appetite of stags in the puberty age. Herein, at least one of 17β-decanoate-4-estrene-3-one and 17β-cyclohexylpropionate-4-estrene-3-one, each in the effective dose, is administered to the stags in the puberty age.

Each dose of at least one of 17β-decanoate-4-estrene-3-one and 17β-cyclohexylpropionate-4-estrene-3-one is preferably 100 mg per 1 kg of the weight of the stag, more preferably 0.1 mg to 10 mg and much more preferably 0.5 mg to 5 mg.

The administration of 17β-decanoate-4-estrene-3-one and 17β-cyclohexylpropionate-4-estrene-3-one is carried out by an oral intake or an injection.

Further, the present invention provides a method of promoting the growth of stag's horn, characterized in that at least one of 17β-decanoate-4-estrene-3-one and 17β-cyclohexylpropionate-4-estrene-3-one, each in the effective dose, is administered to the stag in the puberty age, thereby allowing to cut and collect stag's horn more than twice in a year. Preferably, the present invention provides a method of artificially inducing the second stag's horn by administering at least one of 17β-decanoate-4-estrene-3-one and 17β-cyclohexylpropionate-4-estrene-3-one to stags in the puberty age of the fall after cutting the first horn in the summer. This method comprises steps of (1) cutting the first stag's horn, which comings up in the spring and is grown up, in the summer; (2) administering at least one of 17β-decanoate-4-estrene-3-one and 17β-cyclohexylpropionate-4-estrene-3-one to stags in the puberty age of the fall; (3) growing and developing the second stag's horn; and (4) cutting the second stag's horn.

Herein, each dose of at least one of 17β-decanoate-4-estrene-3-one and 17β-cyclohexylpropionate-4-estrene-3-one is preferably 0.1 mg to 100 mg per 1 kg of the weight of the stag, more preferably 0.1 mg to 10 mg and much more preferably 0.5 mg to 5 mg.

BEST MODE FOR CARRYING OUT THE INVENTION

Preferred embodiments of the present invention will be described below with reference to several test Examples.

EXAMPLE 1

Alleviating the Violence and Stimulating the Appetite of Stag in the Puberty Age of the Fall by Administering 17β-decanoate-4-estrene-3-one To 4 stags of elk, each in the weight of 500 kg, which is violent and anorexia in the puberty age of the fall, 17β-decanoate-4-estrene-3-one 500 mg (effective dose corresponding to 1 mg per 1 kg of the weight of stag: "ANABOLIN FORTE" is the trademark manufactured by Alfasan in Nederland and containing 17β-decanoate-4-estrene-3-one 50 mg in a injection product 1 ml; "ANABOLIN FORTE 10 ml" is the trademark imported by BUM-HAN PHARM. in Korea) was intramuscularly-injected. The test results are shown in Table 1.

TABLE 1 the results of alleviating the violence and stimulating the appetite of stag in the puberty age of the fall by administering 17β-decanoate-4-estrene-3-one

| Variety | Weight (kg) | Injection Date | Dose (mg) | Status Before | Status After |
|---|---|---|---|---|---|
| Elk 1 | 500 | 2000.10.2 | 500 | Violent | Alleviating violence Stimulating appetite |
| Elk 2 | 500 | 2000.10.2 | 500 | Violent | Alleviating violence Stimulating appetite |
| Elk 3 | 500 | 2000.10.2 | 500 | Violent | Alleviating violence Stimulating appetite |
| Elk 4 | 500 | 2000.10.2 | 500 | Violent | Alleviating violence Stimulating appetite |

As shown in Table 1, after 17β-decanoate-4-estrene-3-one in the effective dose was intramuscularly injected to stags of elk, each of 1.0 mg/kg in the weight, which is violent and anorexia in the puberty age of the fall, the injected stags were less violent and stimulated in appetite, thereby increasing the intake of feed.

EXAMPLE 2

Alleviating the Violence and Stimulating the Appetite of Stag in the Puberty Age of the Fall by Administering 17β-decanoate-4-estrene-3-one To 8 stags of elk, each in the weight of 500 kg, which is violent and anorexia in the puberty age of the fall, 17β-decanoate-4-estrene-3-one 50 mg, 100 mg, 250 mg, 500 mg, 750 mg, 1,000 mg, 2,500 mg and 5,000 mg (effective doses corresponding to 0.1 mg, 0.2 mg, 0.5 mg, 1.0 mg, 1.5 mg, 2.0 mg, 5.0 mg and 10 mg per 1 kg of the weight of stag: "ANABOLIN FORTE" is the trademark manufactured by Alfasan in Nederland and containing 17β-decanoate-4-estrene-3-one 50 mg in a injection product 1 ml; "ANABOLIN FORTE 1 ml, 2 ml, 5 ml, 10 ml, 15 ml, 20 ml, 50 ml and 100 ml" is the trademark imported by BUM-HAN PHARM. in Korea) were injected-injected. The test results are shown in Table 2.

TABLE 2 the results of alleviating the violence and stimulating the appetite of stag in the puberty age of the fall by administering 17β-decanoate-4-estrene-3-one

| Variety | Weight (kg) | Dose (mg) | Status Before | Status After |
|---|---|---|---|---|
| Elk 5 | 500 | 50 | Violent | Alleviating violence Stimulating appetite |
| Elk 6 | 500 | 100 | Violent | Alleviating violence Stimulating appetite |
| Elk 7 | 500 | 250 | Violent | Alleviating violence Stimulating appetite |
| Elk 8 | 500 | 500 | Violent | Alleviating violence Stimulating appetite |
| Elk 9 | 500 | 750 | Violent | Alleviating violence Stimulating appetite |
| Elk 10 | 500 | 1,000 | Violent | Alleviating violence Stimulating appetite |
| Elk 11 | 500 | 2,500 | Violent | Alleviating violence Stimulating appetite |
| Elk 12 | 500 | 5,000 | Violent | Alleviating violence Stimulating appetite |

As shown in Table 2, after 17β-decanoate-4-estrene-3-one in the effective doses corresponding to 0.1 mg, 0.2 mg, 0.5 mg, 1.0 mg, 1.5 mg, 2.0 mg, 5.0 mg and 10 mg per 1 kg of the weight of stag were injected-injected to stags of elk, each in the weight of 500 kg, which is violent and anorexia in the puberty age of the fall, the injected stags were less violent and stimulated in appetite, thereby increasing the intake of feed.

EXAMPLE 3

Promoting the Growth of Stag's Horn by Administering 17β-decanoate-4-estrene-3-one To 4 stags of elk, of which the first horn coming up in the spring and growing cut in the summer, each in the weight of 500 kg, 17β-decanoate-4-estrene-3-one 500 mg (effective dose corresponding to 1 mg per 1 kg of the weight of stag: "ANABOLIN FORTE" is the trademark manufactured by Alfasan in Nederland and containing 17β-decanoate-4-estrene-3-one 50 mg in a injection product 1 ml; "ANABOLIN FORTE 10 ml" is the trademark imported by BUM-HAN PHARM. in Korea) was injected-injected. The test results are shown in Tables 3 and 4.

[Table 3] The Results of Promoting the Growth of Stag's Horn by Administering 17β-decanoate-4-estrene-3-one

| Injection Date | Variety | Growth and development progress of the second stag's horn (cm) The number of days After administration (day) | | | | | | | | | | |
|---|---|---|---|---|---|---|---|---|---|---|---|---|
| | | 0 | 10 | 20 | 30 | 40 | 50 | 60 | 70 | 80 | 90 | 100 |
| Oct. 2, 1999 | Elk 21 | 0 | 0 | 0 | 0.5 | 30 | 40 | 60 | 80 | 90 | 100 | 100 |
| Oct. 2, 2000 | Elk 21 | 0 | 0 | 0 | 0.5 | 30 | 40 | 60 | 80 | 100 | 110 | 110 |
| Oct. 2, 1999 | Elk 22 | 0 | 0 | 0 | 0.5 | 30 | 40 | 60 | 80 | 100 | 110 | 110 |
| Oct. 2, 2000 | Elk 22 | 0 | 0 | 0 | 0.5 | 30 | 40 | 60 | 80 | 100 | 120 | 120 |

As shown in Table 3, after 17β-decanoate-4-estrene-3-one in the effective dose corresponding to 1 mg per 1 kg of the weight of stag was intramuscularly injected to stags of elk, each in the weight of 500 kg, of which the first horn coming up in the spring and growing cut in the summer, the second stag's horn come up after 30 days from administration and was grown up by 3 cm per a day. Then, after 40 days from administration, the second stag's horn was grown up to approximately 30 cm, and after 80 to 90 days from administration, the second stag's horn was grown up to approximately 100 to 120 cm.

TABLE 4 the results of production amount of stag's horn by administering 17β-decanoate-4-estrene-3-one

| | | Production amount of stag's horn (kg) | |
|---|---|---|---|
| Injection Date | Variety | The first horn collected in the fall | The second horn collected in the next spring |
| 1999.10.2 | Elk 21 | 12 kg | 9.6 kg |
| 2000.10.2 | Elk 21 | 15 kg | 12 kg |
| 1999.10.2 | Elk 22 | 15 kg | 12 kg |
| 2000.10.2 | Elk 22 | 12 kg | 9.6 kg |

As shown in Table 4, after 17β-decanoate-4-estrene-3-one in the effective dose corresponding to 1 mg per 1 kg of the weight of stag was injected-injected to stags of elk, each in the weight of 500 kg, of which the first horn coming up in the spring and grown up cut in the summer, the production amount of the first stag's horn was 10 to 15 kg. However, the production amount of the second stag's horn was about 80% of that of the first stag's horn.

EXAMPLE 4

Composition Analysis Between the First Stag's Horn and the Second Stag's Horn

To a stag of elk in the weight of 500 kg, of which the first horn coming up in the spring of 2000 and grown up cut in the summer, 17β-decanoate-4-estrene-3-one 500 mg (effective dose corresponding to 1 mg per 1 kg of the weight of stag: "ANABOLIN FORTE" is the trademark manufactured by Alfasan in Nederland and containing 17β-decanoate-4-estrene-3-one 10 mg in a injection product 1 ml; "ANABOLIN FORTE 10 ml" is the trademark imported by BUM-HAN PHARM. in Korea) was injected-injected. The test results of composition analysis between the first stag's horn and the second stag's horn are shown in Table 5.

TABLE 5 composition ingredients of the second horn of elk 22 injected dated October 2, 2000

| Status | Type | Moisture | Protein | Lipid | Ash content | Cholesterol |
|---|---|---|---|---|---|---|
| Grinding | First | 6.81 | 66.65 | 3.21 | 22.72 | 0.61 |
| | Second | 7.58 | 66.04 | 3.11 | 22.64 | 0.63 |
| Upper tip | First | 2.59 | 68.68 | 3.89 | 24.19 | 0.65 |
| | Second | 2.61 | 69.02 | 3.72 | 24.01 | 0.64 |

As shown in Table 5, the composition ingredient of the first stag's horn that was collected in the summer was almost identical with that of the second stag's horn that was treated by administering 17β-decanoate-4-estrene-3-one and collected in the winter. Particularly, two types of the stag's horn were almost the same to each other in ash content determining the physical properties and the grade of the stag's horn.

EXAMPLE 5

Promoting State of the Growth of Stag's Horn in Accordance with Doses of 17β-decanoate-4-estrene-3-one To 8 stags of elk, each in the weight of 500 kg, of which the first horn coming up in the spring and grown up cuts in the summer, 17β-decanoate-4-estrene-3-one 50 mg, 100 mg, 250 mg, 500 mg, 750 mg, 1,000 mg, 2,500 mg and 5,000 mg (effective doses corresponding to 0.1 mg, 0.2 mg, 0.5 mg, 1.0 mg, 1.5 mg, 2.0 mg, 5.0 mg and 10 mg per 1 kg of the weight of stag: "ANABOLIN FORTE" is the trademark manufactured by Alfasan in Nederland and containing 17β-decanoate-4-estrene-3-one 50 mg in a injection product 1 ml; "ANABOLIN FORTE 1 ml, 2 ml, 5 ml, 10 ml, 15 ml, 20 ml, 50 ml and 100 ml" is the trademark imported by BUM-HAN PHARM. in Korea) were injected-injected. Then, the growth of the second stag's horn was observed in the fall. The test results are shown in Table 6.

TABLE 6 promoting state of the growth of stag's horn in accordance with doses of 17β-decanoate-4-estrene-3-one

| | | | Production amount of stag's horn (kg) | |
|---|---|---|---|---|
| Variety | Weight (kg) | Dose (mg) | The first horn collected in the summer | The second horn collected in the next spring |
| Elk 31 | 500 | 50 | 15 | 5 |
| Elk 32 | 500 | 100 | 15 | 5 |
| Elk 33 | 500 | 250 | 15 | 12 |
| Elk 34 | 500 | 500 | 15 | 12 |
| Elk 35 | 500 | 750 | 15 | 12 |
| Elk 36 | 500 | 1,000 | 15 | 12 |
| Elk 37 | 500 | 2,500 | 15 | 5 |
| Elk 38 | 500 | 5,000 | 15 | 5 |

As shown in Table 6, after 17β-decanoate-4-estrene-3-one in the effective doses corresponding to 0.1 mg, 0.2 mg, 0.5 mg, 1.0 mg, 1.5 mg, 2.0 mg, 5.0 mg and 10 mg per 1 kg of the weight of stag, were respectively injected-injected to each stag of elk in the weight of 500 kg, of which the first horn coming up in the spring and grown up cuts in the summer, the growth of stag's horn was promoted by administering 17β-decanoate-4-estrene-3-one.

EXAMPLE 6

Alleviating the Violence and Stimulating the Appetite of Stag in the Puberty Age of the Fall by Administering 17β-cyclohexylpropionate-4-estrene-3-one Example 6 was the same as Example 1, except that Example 6 substituted 17β-cyclohexylpropionate-4-estrene-3-one for 17β-decanoate-4-estrene-3-one. Herein, the test results of Example 6 using 17β-cyclohexylpropionate-4-estrene-3-one were the same as those of Example 1 using 17β-decanoate-4-estrene-3-one.

EXAMPLE 7

Alleviating the Violence and Stimulating the Appetite of Stag in the Puberty Age of the Fall in Accordance with Doses of 17β-cyclohexylpropionate-4-estrene-3-one Example 7 was the same as Example 2, except that Example 7 substituted 17β-cyclohexylpropionate-4-estrene- 3-one for 17β-decanoate-4-estrene-3-one. Herein, the test results of Example 7 using 17β-cyclohexylpropionate-4-estrene-3-one were the same as those of Example 2 using 17β-decanoate-4-estrene-3-one.

EXAMPLE 8
Promoting the Growth of Stag's Horn by Administering 17β-cyclohexylpropionate-4-estrene-3-one Example 8 was the same as Example 3, except that Example 8 substituted 17β-cyclohexylpropionate-4-estrene-3-one for 17β-decanoate-4-estrene-3-one. Herein, the test results of Example 8 using 17β-cyclohexylpropionate-4-estrene-3-one were the same as those of Example 3 using 17β-decanoate-4-estrene-3-one.

EXAMPLE 9
Promoting State of the Growth of Stag's Horn in Accordance with Doses of 17β-cyclohexylpropionate-4-estrene-3-one Example 9 was the same as Example 5, except that Example 9 substituted 17β-cyclohexylpropionate-4-estrene-3-one for 17β-decanoate-4-estrene-3-one. Herein, the test results of Example 9 using 17β-cyclohexylpropionate-4-estrene-3-one were the same as those of Example 5 using 17β-decanoate-4-estrene-3-one.

EXAMPLE 10
Alleviating the Violence and Stimulating the Appetite of Stag in the Puberty Age of the Fall by Administering a Compound of 17β-decanoate-4-estrene-3-one and 17β-cyclohexylpropionate-4-estrene-3-one Example 10 was the same as Example 2, except that Example 9 substituted a compound of 17β-decanoate-4-estrene-3-one and 17β-cyclohexylpropionate-4-estrene-3-one for 17β-decanoate-4-estrene-3-one. Herein, the test results of Example 10 using a compound of 17β-decanoate-4-estrene-3-one and 17β-cyclohexylpropionate-4-estrene-3-one were the same as those of Example 2 using 17β-decanoate-4-estrene-3-one.

EXAMPLE 11
Promoting the Growth of Stag's Horn by Administering a Compound of 17β-decanoate-4-estrene-3-one and 17β-decanoate-4-estrene-3-one Example 11 was the same as Example 3, except that Example 9 substituted a compound of 17β-decanoate-4-estrene-3-one and 17β-cyclohexylpropionate-4-estrene-3-one for 17β-decanoate-4-estrene-3-one. Herein, the test results of Example 11 using a compound of 17β-decanoate-4-estrene-3-one and 17β-cyclohexylpropionate-4-estrene-3-one were the same as those of Example 3 using 17β-decanoate-4-estrene-3-one.

Although the preferred embodiments of the present invention have been described in detail hereinabove, it should be understood that many variations and/or modifications of the basic inventive concepts herein taught which may appear to those skilled in the art will still fall within the spirit and scope of the present invention as defined in the appended claims.

Industrial Applicability

Accordingly, the present invention provides a method of alleviating the violence and stimulating the appetite of stags in the puberty age of the fall and to a method of allowing to cut and collect more than twice stag's horn by administering 17β-decanoate-4-estrene-3-one and/or 17β-cyclohexylpropionate-4-estrene-3-one, thereby increasing the domestic self-supply rate of the stag's horn and the income of the breeders, preventing outflow of foreign currency and improving international competitive power of our domestic breeders.

What is claimed is:

1. A method of alleviating the violence and stimulating the appetite of stags in the puberty age, said method characterized in that at least one of 17β-decanoate-4-estrene-3-one and 17β-cyclohexylpropionate-4-estrene-3-one, each in the effective dose, is administered to said stags in the puberty age.

2. The method of alleviating the violence and stimulating the appetite of stags in the puberty age claimed in claim 1, wherein each dose of 17β-decanoate-4-estrene-3-one and 17β-cyclohexylpropionate-4-estrene-3-one is 0.1 mg to 10 mg per 1 kg of the weight of said stag.

3. The method of alleviating the violence and stimulating the appetite of stags in the puberty age claimed in claim 1, wherein the administration is carried out by an oral intake or an injection.

4. A method of promoting the growth of stag's horn in the puberty age, said method characterized in that at least one of 17β-decanoate-4-estrene-3-one and 17β-cyclohexylpropionate-4-estrene-3-one, each in the effective dose, is administered to said stag in the puberty age.

5. The method of promoting the growth of stag's horn in the puberty age claimed in claim 4, wherein each dose of 17β-decanoate-4-estrene-3-one and 17β-cyclohexylpropionate-4-estrene-3-one is 0.1 mg to 10 mg per 1 kg of the weight of said stag.

6. The method of promoting the growth of stag's horn in the puberty age claimed in claim 4, wherein the administration is carried out by an oral intake or an injection.

7. The method of promoting the growth of stag's horn in the puberty age claimed in claim 4, wherein the stag's horn is cut and collected twice in one year from the stag.

* * * * *